(12) United States Patent
Mason

(10) Patent No.: US 6,930,075 B1
(45) Date of Patent: Aug. 16, 2005

(54) FATTY ACID-BASED HERBICIDAL COMPOSITION

(75) Inventor: Wenda Mason, Brentwood Bay (CA)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 09/692,797

(22) Filed: Oct. 20, 2000

Related U.S. Application Data

(63) Continuation of application No. 08/309,559, filed on Sep. 20, 1994, now abandoned, which is a continuation of application No. 08/111,282, filed on Aug. 24, 1993, now abandoned, which is a continuation of application No. 07/799,661, filed on Nov. 21, 1991, now abandoned, which is a continuation of application No. 07/608,306, filed on Nov. 2, 1990, now abandoned.

(51) Int. Cl.$^7$ .................. A01N 57/12; A01N 57/20; A01N 37/02; A01N 37/06
(52) U.S. Cl. .................. 504/127; 504/126; 504/142; 504/206; 504/320
(58) Field of Search ................ 504/127, 142, 504/206, 320, 126

(56) References Cited

U.S. PATENT DOCUMENTS

| | | | |
|---|---|---|---|
| 2,622,975 A | 12/1952 | Zimmerman et al. | |
| 2,626,862 A | 1/1953 | Zimmerman et al. | |
| 3,455,675 A | 7/1969 | Irani | |
| 3,556,762 A | 1/1971 | Hamm | |
| 3,645,716 A | 2/1972 | Rutkowski | |
| 3,799,758 A | 3/1974 | Franz | |
| 3,868,407 A | 2/1975 | Franz et al. | |
| 3,888,915 A | 6/1975 | Alt | |
| 3,929,450 A | 12/1975 | Hamm et al. | |
| 3,977,860 A * | 8/1976 | Franz | |
| 3,988,142 A | 10/1976 | Franz | |
| 4,134,754 A | 1/1979 | Hoffman | |
| 4,140,513 A | 2/1979 | Prill | |
| 4,147,719 A | 4/1979 | Franz | |
| 4,159,901 A | 7/1979 | Beestman et al. | |
| 4,315,765 A | 2/1982 | Large | |
| 4,341,549 A | 7/1982 | Large et al. | |
| 4,376,644 A | 3/1983 | Large | |
| 4,384,880 A | 5/1983 | Large | |
| 4,397,676 A | 8/1983 | Bakel | |
| 4,405,531 A | 9/1983 | Franz | |
| 4,436,547 A * | 3/1984 | Sampson | |
| 4,437,874 A | 3/1984 | Large | |
| 4,440,562 A | 4/1984 | Prill | |
| 4,445,927 A | 5/1984 | Gimesi et al. | |
| 4,464,194 A | 8/1984 | Prisbylla | |
| 4,475,942 A | 10/1984 | Bakel | |
| 4,481,026 A | 11/1984 | Prisbylla | |
| 4,525,202 A | 6/1985 | Large et al. | |
| 4,528,023 A | 7/1985 | Ahle | |
| 4,626,274 A | 12/1986 | Hausmann et al. | |
| 4,834,908 A | 5/1989 | Hazen et al. | |
| 4,975,110 A | 12/1990 | Puritch et al. | |
| 5,035,741 A | 7/1991 | Puritch et al. | |
| 5,037,654 A | 8/1991 | Puritch et al. | |
| 5,078,782 A | 1/1992 | Nielsen et al. | |
| 5,147,444 A * | 9/1992 | Decor et al. | 504/127 |
| 5,196,044 A | 3/1993 | Caulder et al. | |
| 5,397,766 A | 3/1995 | Dexter | |
| 5,994,269 A | 11/1999 | Bugg et al. | |
| 6,218,336 B1 * | 4/2001 | Coleman | 504/118 |
| 6,468,944 B1 | 10/2002 | Bugg et al. | |
| 6,503,869 B1 | 1/2003 | Beste et al. | |
| 6,509,297 B1 * | 1/2003 | Coleman | 504/127 |

FOREIGN PATENT DOCUMENTS

| | | |
|---|---|---|
| AU | 586293 | 5/1987 |
| EP | 577914 * | 1/1994 |
| FR | 2589328 | 5/1987 |
| GB | 2169806 | 8/1986 |
| JP | 59/193804 | 11/1984 |
| JP | 59/193809 | 11/1984 |
| JP | 59/199608 | 11/1984 |
| JP | 59/199609 | 11/1984 |
| JP | 61-106501 | 5/1986 |

(Continued)

OTHER PUBLICATIONS

Grossbard, E. et al., The Herbicide Glyphosate (London, Butterworths, 1985), pp. 3-4 225-226.*

(Continued)

Primary Examiner—John Pak
(74) Attorney, Agent, or Firm—Senniger Powers; Joseph A. Schaper

(57) ABSTRACT

Disclosed is a herbicidal composition which combines two known active ingredients at concentrations of the individual active ingredients below the level generally necessary for the individual ingredients to exhibit herbicidal activity. The herbicidal activity of the disclosed composition is greater than that of either of the individual active ingredients used alone. One of the active ingredients is a fatty acid based composition selected from caprylic acid, pelargonic acid, capric acid, undecanoic acid, 10-undecanoic acid, lauric acid, oleic acid, salts thereof and mixtures thereof. In addition, other fatty acid or fatty acid salt mixtures may be used, such as soybean fatty acid or coconut fatty acid. This component is present at a concentration range of about 0.1 to 3.0 percent by weight. The other active ingredient is a glyphosate-based herbicidal active ingredient, e.g., the isopropyl amine salt of N-(phosphonomethyl) glycine, present at about 0.08 to 1.0 percent by weight.

11 Claims, No Drawings

FOREIGN PATENT DOCUMENTS

| | | | |
|---|---|---|---|
| JP | 61-289004 | | 12/1986 |
| JP | 63-080846 | | 4/1988 |
| WO | 89/03178 | * | 4/1989 |
| WO | 90/07275 | * | 7/1990 |
| WO | WO 92/06596 | | 4/1992 |
| WO | WO 92/11764 | | 7/1992 |

OTHER PUBLICATIONS

Wells, A.J., "Adjuvants, glyphosate efficacy and post-spraying rainfall," Plant Protection Quarterly, vol. 4(4), 1989, pp. 156-164.*

"Effect of salt Additives on Activity and Movement of Glyphosate and MSMA in Purple Nutsedge" Technical Bulletin 140 of the Mississippi Agricultural and Forestry Experiment Station, Apr. 1987, Mississippi State University, Mississippi State, MS 39762.

Turner "The Herbicide Glyophosate", Grossbard and Atkinson, editors, Butterworth & Co., Ltd., pp. 221-240 (1985).

Grant & Hack's Chemical Dictionary, Grant et al. editors, 5th Ed. McGraw Hill Book Co., NY (1987) p. 230.

U.S. Patent and Trademark Office Patent Classification Definition: (1990).

The Agrochemicals Handbook, 2nd Edition, Hartley and Kidd, editors; The Royal Society of Chemistry, Nottingham, England, 1987, pp. A045, A138.

Schilling et al. J. Aquat. Plant. Manage., 28:23-27 (1990).

* cited by examiner

FATTY ACID-BASED HERBICIDAL COMPOSITION

This application is a Continuation of Ser. No. 08/309,559, filed on Sep. 20, 1994, now abandoned, which is a Continuation of Ser. No. 08/111,282, filed on Aug. 24, 1993, now abandoned, which is a Continuation of Ser. No. 07/799,661, filed on Nov. 21, 1991, now abandoned, which is a Continuation of Ser. No. 07/608,306, filed on Nov. 2, 1990, now abandoned.

BACKGROUND OF THE INVENTION

This invention relates to herbicidal compositions which are effective, economical and environmentally compatible. More particularly, an improved herbicidal composition has been obtained by combining a fatty acid-based active ingredient with a glyphosate-based active ingredient.

Herbicides are widely used to control the rate of growth or to cause mortality in unwanted or undesirable plant species. Among the most widely used herbicides are those which are petrochemical-based. Although quite effective, many petrochemical-based herbicides are considered to pose hazards to the environment, as well as to humans, animals and aquatic life.

Due to concerns for such hazards posed by petrochemical-based herbicides, several environmentally compatible herbicides have been developed. Fatty acid based compounds having between eight and eighteen carbon atoms serve as an example of one class of environmentally compatible herbicides. These compounds occur naturally in soil and decompose quite rapidly (i.e., within about 1–3 days) within soil. An exemplary fatty acid-based herbicidal compositions is commercially available from Safer, Inc. under the trademark SHARPSHOOTER. This herbicidal composition utilizes an active ingredient which is a mixture of partially saponified fatty acids. Other fatty acid-based herbicidal compositions are disclosed in U.S. patent application Ser. Nos. 421,146 and 421,376, both of which were filed on Oct. 13, 1989.

Such fatty acid-based herbicides are quite effective for most applications. However, like most pesticides, they are not well suited for all applications. For example, these compositions are not able to translocate and are thus only effective on the plant tissue which is contacted by the herbicidal composition. Also, because such compositions are used in relatively high concentrations of active ingredient, i.e., 3 to 6 percent, their use can be costly.

One petrochemical-based herbicide which apparently exhibits minimal environmental impact is a glyphosate-based composition. This compound is an effective, broad spectrum herbicide which has the ability to translocate within plant systems. Glyphosate-based herbicides can be expensive to use, and typically must be applied at concentrations in the range of 1 to 2 percent. One potential drawback to the use of glyphosate-based compounds is that they do not occur naturally and have an average half-life in soil slightly less than 60 days.

While fatty acid based herbicides are advantageous due to their environmental compatibility, they lack the ability to translocate, and must be used in relatively high concentrations. Glyphosate-based herbicides must also be used in relatively high concentrations and are relatively expensive. Moreover, it would be desirable to provide a herbicidal composition which combines the beneficial features of these herbicides, while reducing the amounts of non-naturally-occurring compounds, such as glyphosate, which are environmentally released.

It is thus an object of the invention to provide an effective, broad spectrum herbicide which is environmentally compatible and economically feasible. Another object is to provide a herbicide which has the advantages of the fatty acid-based herbicide, but which also has the ability to translocate. An additional object of the invention is to provide an effective herbicidal composition with improved efficacy. A further object of the invention is to provide a herbicidal composition which combines two known active ingredients in such a way that the concentration of each of the individual components is present at levels less than what is recommended for herbicidal activity. It is also an object of the invention to provide an effective herbicide while at the same time reducing the pesticide load in the environment. Other objects will be apparent to those skilled in the art upon reading the following disclosure.

SUMMARY OF THE INVENTION

The present invention provides an effective, environmentally compatible herbicidal composition which combines two known active ingredients such that each is present at a concentration below what is recommended for herbicidal activity of each ingredient alone. The composition combines a fatty acid-based herbicide with a glyphosate-based herbicide. The fatty acid component may be a fatty acid such as caprylic acid, pelargonic acid, capric acid, undecanoic acid, 10-undecanoic acid, lauric acid, oleic acid and mixtures of these fatty acids and other fatty acid mixtures such as soybean fatty acid and coconut fatty acid. In another embodiment salts, or mixtures of various salts of these fatty acids may be used as one herbicidal active ingredient. The glyphosate component preferably is N-(phosphonomethyl) glycine, its derivatives or the salts thereof. The fatty acid or fatty acid salt component is present in the range of 0.1 to 3.0 percent by weight of the composition while the glyphosate component is present at 0.08 to 2.0 percent by weight of the composition.

DETAILED DESCRIPTION OF THE INVENTION

The herbicidal composition of the invention, as noted above, comprises a combination of two active ingredients in an aqueous solution. One active ingredient comprises one or a mixture of fatty acids or salts of fatty acids. The other active ingredient is a glyphosate-based compound such as N-(phosphonomethyl)glycine. The concentration range of fatty acid active ingredient is about 0.1 to 3 percent by weight and the concentration range of glyphosate active ingredient component is about 0.08 to 2.0% by weight.

The fatty acid component of this herbicidal composition can be one or a mixture of fatty acids. The fatty acids which may be used include caprylic acid, pelargonic acid, capric acid, undecanoic acid, 10-undecanoic acid, lauric acid, oleic acid and mixtures thereof. Other fatty acid mixtures such as soybean fatty acid and coconut fatty acid (which are described below) may also form the fatty acid component. Pelargonic acid is a preferred fatty acid-based active ingredient. However, in other embodiments mixtures of fatty acids such as mixtures of pelargonic, capric and lauric acids; or a mixture of capric and lauric acids may be used as well.

Soybean fatty acids comprise a mixture of the following fatty acids in the following percentages by weight: 0.5% lauric acid, 0.5% myristic acid, 12% palmitic acid, 4% stearic acid, 25% oleic acid, 52% linoleic acid, and 6% linolenic acid. Coconut fatty acids comprise a mixture of the following fatty acids in the following percentages by weight: 7% caprylic acid, 6% capric acid, 50% lauric acid, 18% myristic acid, 8.5% palmitic acid, 3% stearic acid, 6% oleic acid, 1% linoleic acid and 0.5% linolenic acid.

An exemplary non-saponified fatty acid active ingredient is pelargonic acid. Also, a mixture of pelargonic acid and capric acid, at a 1:1 ratio, serves as an effective saponified active ingredient.

Various fatty acid salts or mixtures of fatty acid salts may also be used as the fatty acid component of the herbicidal composition of this invention. These include sodium, potassium and other metal salts, as well as ammonium salts of caprylic acid, pelargonic acid, capric acid, undecanoic acid, 10-undecanoic acid, lauric acid, oleic acid, mixtures thereof and other fatty acid salt mixtures such as soybean fatty acid and coconut fatty acid.

Among the most preferred fatty acid salts are the sodium and potassium salts of pelargonic acid.

Other exemplary fatty acid salt mixtures which may be used as an active ingredient in the present herbicidal composition include the partial or complete sodium or potassium salts of pelargonic, capric acid and coconut fatty acid in a ratio of 1:1:2. Another exemplary saponified fatty acid mixture which may be used as an active ingredient in this herbicidal composition includes a 1:1 mixture of the partial or complete sodium or potassium salts of soybean and coconut fatty acids.

As noted above, a variety of combinations of fatty acids or fatty acid salts may be used in preparing the fatty acid active ingredient of the present herbicidal composition. The fatty acid active ingredient may also include a variety of surfactants, emulsifiers and other formulation enhancers. One of ordinary skill in the art will easily be able to decide whether any such compounds are necessary, and if so, to choose the desired compounds. By way of example, however, exemplary surfactants include quarternary ammonium salts, ethoxylated phosphate esters, polyoxyethylene derivatives of fatty acid partial esters of sorbitol anhydrides, castor oil ethoxylate, nonyl phenyl ethoxylates, isopropyl alcohol and mixtures thereof. Exemplary quaternary ammonium salt compounds are commercially available under the trademarks "Ethoquad" and "Arquad" from Akzo America, Inc. of Chicago, Ill. Exemplary emulsifiers include those which are alkylaryl sulfonate-based polyoxyethylene derivatives of fatty acid and partial esters of sorbitol anydrides. Commercially available examples include those sold under the trademark "Atlox" and "Tween" by Atkemix, Inc. and those sold under the trademark "Emsorb" by Quantum Chemicals of Cincinnati, Ohio. Formulation enhancers may include alcohols and oils such as terpenoids, triglycerides and mineral oils.

A number of exemplary formulations which may be used as the fatty acid active ingredient of this invention are disclosed in U.S. patent application Ser. Nos. 421,146 and 421,376 both of which were filed on Oct. 13, 1989 and are hereby incorporated by reference. However it is understood that the fatty acid active ingredient may comprise many combinations of the fatty acids or saponified fatty acids noted above, together with the surfactants, emulsifiers, and formulation enhancers noted above and others well known in the art. One example of fatty acid active ingredient formulation comprises the following components:

16.6% coconut fatty acid
    8.3% pelargonic acid
    8.3% capric acid
    9.78% potassium hydroxide (45% solution)
    30.0% denatured alcohol
    30.0% water The other active ingredient of the herbicidal composition is the glyphosate-based compound. As used herein the term "glyphosate-based" includes N-(phosphonomethyl) glycine and various related compounds and salts as disclosed in U.S. Pat. No. 3,799,758, which is incorporated herein by reference.

Glyphosate-based compounds typically have the general formula:

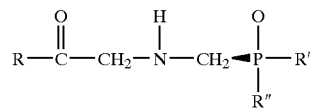

In the above formula R, R' and R" can be —OH, halogen or —SH groups. Various other glyphosate-based compounds are described in U.S. Pat. No. 3,799,758 which is hereby incorporated by reference. Among the most preferred glyphosate-based compounds is N-(phosphonomethyl) glycine in which R, R' and R" are all hydroxy groups.

In addition to the glyphosate-based compounds described above, the glyphosate-based component of this herbicidal composition may also include various salts of glyphosate-based compounds. Such salts may be prepared by the partial or complete neutralization of the acid with the appropriate base, carbonate, ammonia or organic amine. One preferred salt of a glyphosate-based compound is the isopropyl amine salt of N-(phosphonomethyl)glycine.

The glyphosate-based component may or may not be formulated with various surfactants. One of ordinary skill in the art will easily be able to decide whether surfactants are necessary, and if so, to choose the necessary surfactants.

Exemplary glyphosate-based compounds are commercially available from Monsanto Company of St. Louis, Mo. under the trademarks ROUNDUP, ACCORD, HONCHO, RANGER, and RODEO.

The glyphosate-based component of the herbicidal composition may be present in the composition at a concentration range of about 0.08 to 2.0% by weight. The preferred concentration range is about 0.1 to 1.0% by weight. If used alone, the preferred concentration range would have little or no herbicidal efficiency since the recommended application concentration is in the range of 1 to 2 percent by weight. Similarly, the fatty acid may be used in a concentration range of about 0.1 to 3.0 percent by weight. A more preferred concentration range for the fatty acid active ingredient is 0.5 to 1.0%. Which is below the concentration range of 3–6% ordinarily necessary to achieve herbicidal activity.

The herbicidal composition of this invention may be prepared by adding the desired amount of the glyphosate-based active ingredient to the required amount of water and mixing thoroughly. The desired amount of fatty acid (saponified or non-saponified) active ingredient formulation is then added and thoroughly mixed into the formulation. This formulation may be pre-formulated so as to form a ready-to-use composition, or may also be prepared just prior to use by tank mixing the two components. In some instances a pre-formulated, ready-to-use composition may require agitation immediately prior to use.

The present herbicidal compositions are foliar applied, nonselective herbicides which may be sprayed upon unwanted weeds and grasses. These herbicidal compositions may be provided in a ready-to-use formulation or in a concentrated formulation which must be diluted with water before application. The formulation applied to unwanted weeds and grasses typically contains in the range of approximately 0.1 to 3 percent fatty acid component and 0.08 to 2.0 glyphosate-based component. More preferably, the fatty acid component is present at 0.5–1.0% and the glyphosate-based component is present at 0.1–1.0%.

The herbicidal compositions of the invention are effective and environmentally compatible. They are broad-spectrum, non-selective herbicides useful in crop, non-crop, aquatic, and domestic weed control, especially in environmentally sensitive areas where reduced pesticide loads are desirable. The compositions are effective on most weed species and are applied as postemergence sprays to foliage of vegetation to be controlled. One advantage of these compositions is that they have the ability to translocate. The carrier volumes are those recommended for glyphosates (47 to 374 l/ha, 5 to 40 gpa). Typically, 7 to 14 days are required before evidence of phytotoxicity or plant mortality appears.

The present composition is quite effective on perennial species, and on annual or biennial species of grasses, sedges, and broadleaf weeds.

The following non-limiting examples serve to further describe the invention.

EXAMPLE 1

Three species of weed, used in each test: *Hypochoeris radicata* (false dandelion), *Sinapis, arvensis* (wild mustard), and *Avena sativa* (oats), were grown in a greenhouse facility in 5.5 cm square pots using a potting soil mix comprising peat, vermiculite, sand, and 4-10-10 fertilizer. Water-soluble 20-20-20 fertilizer was used as a supplement for the plants as required. The plants were selected for use based on uniformity and quality and were potted separately. One plant per pot each of *H. radicata* (6–10 leaves) and *S. arvensis* (4–6 leaves) were used. Six to eight plants of *A. sativa* (2–4 leaves) were used per pot. After spraying with a herbicidal composition (as described below) the pots were arranged in a randomized complete block design in sub-irrigated watering trays. Six to ten replicates (pots) were used per treatment.

Herbicidal treatments were applied using a spray chamber fitted with a TeeJet 8006E flat fan nozzle (available from Spraying Systems Co., Wheaton, Ill.), calibrated to spray at a volume of 60 gpa at 40 psi. Treatment solutions were freshly prepared for each experiment. Plant damage was assessed at 10 to 14 days after treatment using a pre-transformed 0–10 rating scale (0 representing no damage, 10 representing plant death) in accordance with the procedure outlined in *Statistical Methods in Agricultural Research*, Little, T. M. et al, J. Wiley and Sons, 1975, pp. 119–120, 218.

The results of these experiments are shown in the tables which follow.

TABLE I

| | | Phytotoxicity (%) | | | | |
|---|---|---|---|---|---|---|
| | | H. radicata | | S. arvensis | | A. sativa | |
| | Herbicide | Observed | Expected | Observed | Expected | Observed | Expected |
| 1. | Round-Up* (0.1%) | 22 | | 1 | | 4 | |
| | Formulation A** (0.1%) | 0 | | 0 | | 4 | |
| | Combination | 28 | 22 | 18 | 1 | 3 | 8 |
| 2. | Round-Up (0.1%) | 22 | | 1 | | 4 | |
| | Formulation A (0.5%) | 1 | | 0 | | 4 | |
| | Combination | 71 | 23 | 88 | 1 | 10 | 8 |
| 3. | Round-Up (0.1%) | 22 | | 1 | | 4 | |
| | Formulation A** (1.0%) | 2 | | 1 | | 6 | |
| | Combination | 64 | 24 | 39 | 2 | 58 | 10 |

*Round-Up is commercially available from Monsanto Company. Its active ingredient is the isopropylamine salt of N-(phosphonomethyl) glycine.
**Formulation A is a mixture of potassium pelargonate, potassium caprate and potassium laurate, in ratios of 1:1:2, used in this experiment at total active ingredient concentrations of 0.1, 0.5 an 1.0 percent by weight.

EXAMPLE 2

In a greenhouse facility four plant species were grown in 5.5 cm square pots using a potting soil mix comprising peat, vermiculite, sand and 4-10-10 fertilizer. Water soluble 20-20-20 fertilizer was used as a supplement for the plants as required. The plant species used were corn, oats, radish and morningglory. The plants were selected for use based on uniformity and quality. The corn plants used were in the 3 to 4 leaf stage and two plants were present in each pot. The oats used were in the 2 to 4 leaf stage and four plants were present per pot. The radish plants used were in the 3 to 5 leaf stage and one plant was used per pot. The morningglory were in the 2 to 4 leaf stage with one plant per pot. After spraying with a herbicidal formulation, the pots were arranged in a randomized complete block design in sub-irrigated watering trays, and included a water-treated control treatment. Four replicates (pots) were used for each treatment.

Herbicidal treatments were applied and recorded as in Example 1.

The data obtained are presented in the tables which follow.

TABLE 2

| | | Phytotoxicity (%) | | | | | |
|---|---|---|---|---|---|---|---|
| | | *H. radicata* | | *S. arvensis* | | *A. sativa* | |
| | Herbicide | Observed | Expected | Observed | Expected | Observed | Expected |
| 1. | Round-Up (0.1%) | 22 | | 1 | | 1 | |
| | Sodium pelargonate (0.1%) | 0 | | 0 | | 0 | |
| | Combination | 47 | 22 | 35 | 1 | 2 | 1 |
| 2. | Round-Up (0.1%) | 22 | | 1 | | 1 | |
| | Sodium pelargonate (0.1%) | 0 | | 0 | | 0 | |
| | Combination | 47 | 22 | 80 | 1 | 2 | 1 |
| 3. | Round-Up (0.1%) | 22 | | 1 | | 1 | |
| | Sodium pelargonate (0.1%) | 0 | | 0 | | 1 | |
| | Combination | 56 | 22 | 88 | 2 | 2 | 2 |

TABLE 3

| | | Phytotoxicity (%) | | | | | |
|---|---|---|---|---|---|---|---|
| | | *H. radicata* | | *S. arvensis* | | *A. sativa* | |
| | Herbicide | Observed | Expected | Observed | Expected | Observed | Expected |
| 1. | Round-Up (0.1%) | 0 | | 30 | | 7 | |
| | Potassium pelargonate (0.1%) | 0 | | 0 | | 6 | |
| | Combination | 12 | 0 | 31 | 30 | 8 | 13 |
| 2. | Round-Up (0.1%) | 0 | | 30 | | 7 | |
| | Potassium pelargonate (0.5%) | 0 | | 0 | | 5 | |
| | Combination | 71 | 0 | 42 | 30 | 14 | 12 |
| 3. | Round-Up (0.1%) | 0 | | 30 | | 7 | |
| | Potassium pelargonate (0.5%) | 3 | | 2 | | 7 | |
| | Combination | 46 | 3 | 45 | 32 | 10 | 14 |

TABLE 4

| | | Phytotoxicity (%) | | | | | |
|---|---|---|---|---|---|---|---|
| | | *H. radicata* | | *S. arvensis* | | *A. sativa* | |
| | Herbicide | Observed | Expected | Observed | Expected | Observed | Expected |
| 1. | Round-Up (0.1%) | 90 | | 8 | | 11 | |
| | Formulation B* (0.1%) | 0 | | 0 | | 3 | |
| | Combination | 96 | 90 | 14 | 8 | 8 | 14 |
| 2. | Round-Up (0.1%) | 90 | | 8 | | 11 | |
| | Formulation B (0.5%) | 0 | | 0 | | 3 | |
| | Combination | 99 | 90 | 9 | 8 | 13 | 14 |
| 3. | Round-Up (0.1%) | 90 | | 8 | | 11 | |
| | Formulation B (1.0%) | 0 | | 0 | | 2 | |
| | Combination | 99 | 90 | 13 | 8 | 9 | 13 |

*Formulation B is a 1:1 mixture of soybean and coconut fatty acids used in this experiment at a total active ingredient concentration of 0.1, 0.5 and 1.0% by weight.

TABLE 5

| | | Radish Plants | | | | | | | | | | | | | | | |
|---|---|---|---|---|---|---|---|---|---|---|---|---|---|---|---|---|---|
| | | Days after Treatment | | | | | | | | | | | | | | | |
| | | 2 | 4 | 7 | 9 | 11 | 16 | 18 | 21 | 23 | 25 | 28 | 30 | 32 | 35 | 42 | 46 | 57 |
| 0.2% Round Up | Phyto* | 0 | 0 | 1 | 1.5 | 3.0 | 4.25 | 4.25 | 4.75 | 6.0 | 5.75 | 6.25 | 6.25 | 6.5 | 5.75 | 5.0 | 5.0 | 5.25 |
| | Mortality | 0 | 0 | 0 | 0 | 0 | 0 | 0 | 0 | 0 | 0 | 0 | 0 | 0 | 0 | 0 | 0 | 0 |
| 0.1% C9 Na⁺ Salt | Phyto | 0 | 0 | 0 | 0 | 0 | 0 | 0 | 0 | 0 | 0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 | 0 | 0 | 0 |
| 0.5% C9 Na⁺ Salt | Phyto | 0 | 0 | 0 | 0 | 0 | 0 | 0 | 0 | 0 | 0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 | 0 | 0 | 0 |
| 1.0% C9 Na⁺ Salt | Phyto | 0 | 0 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| | Mortality | 0 | 0 | 0 | 0 | 0 | 0 | 0 | 0 | 0 | 0 | 0 | 0 | 0 | 0 | 0 | 0 | 0 |
| 0.2% R-U** | Phyto | 0 | 0 | 1.0 | 1.5 | 2.0 | 2.25 | 2.75 | 2.75 | 3.5 | 3.25 | 3.25 | 2.75 | 3.25 | 3.25 | 3.5 | 3.5 | 5.0 |

TABLE 5-continued

Radish Plants

| | | Days after Treatment | | | | | | | | | | | | | | | | |
|---|---|---|---|---|---|---|---|---|---|---|---|---|---|---|---|---|---|---|
| | | 2 | 4 | 7 | 9 | 11 | 16 | 18 | 21 | 23 | 25 | 28 | 30 | 32 | 35 | 42 | 46 | 57 |
| 0.1% C9 Na⁺ Salt | Mortality | 0 | 0 | 0 | 0 | 0 | 0 | 0 | 0 | 0 | 0 | 0 | 0 | 0 | 0 | 0 | 0 | 0 |
| 0.2% R-U 0.5% C9 Na⁺ Salt | Phyto | 0 | 0 | 1.0 | 2.5 | 4.0 | 6.0 | 7.0 | 7.0 | 7.25 | 7.0 | 7.25 | 7.0 | 6.75 | 6.75 | 6.75 | 7.0 | 8.25 |
| | Mortality | 0 | 0 | 0 | 0 | 0 | 0 | 0 | 0 | 0 | 0 | 0 | 0 | 0 | 0 | 1/4° | 2/4 | 2/4 |
| 0.2% R-U 1.0% C9 Na⁺ Salt | Phyto | 0 | 0 | 2.0 | 3.0 | 4.5 | 6.5 | 6.5 | 6.25 | 6.75 | 6.5 | 6.50 | 6.75 | 7.0 | 7.0 | 6.5 | 7.0 | 8.25 |
| | Mortality | 0 | 0 | 0 | 0 | 0 | 0 | 0 | 0 | 0 | 0 | 0 | 0 | 0 | 0 | 0 | 0 | 1/4 |

*Phyto = Phytotoxicity (0–10 rating scale)
**R-U = Round-Up
°Denotes 1 of the 4 plants died.

TABLE 6

Morningglory

| | | Days after Treatment | | | | | | | | | | | | | |
|---|---|---|---|---|---|---|---|---|---|---|---|---|---|---|---|
| | | 2 | 4 | 7 | 9 | 11 | 16 | 18 | 21 | 23 | 25 | 28 | 30 | 32 | 35 |
| 0.2% Round Up | Phyto | 0 | 0 | 0.5 | 0.5 | 0.5 | 0.75 | 1.0 | 1.0 | 1.0 | 1.25 | 1.25 | 1.25 | 1.25 | 1.25 |
| | Mortality | 0 | 0 | 0 | 0 | 0 | 0 | 0 | 0 | 0 | 0 | 0 | 0 | 0 | 0 |
| 0.1% C9 Na⁺ Salt | Phyto | 0 | 0 | 0 | 0 | 0 | 0 | 0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 |
| 0.5% C9 Na⁺ Salt | Phyto | 0 | 0 | 0 | 0 | 0 | 0 | 0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 |
| 1.0% C9 Na⁺ Salt | Phyto | 0 | 0 | 0 | 0 | 0 | 0 | 0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 |
| 0.2% R-U 0.1% C9 Na⁺ Salt | Phyto | 0 | 0 | 1.0 | 3.0 | 4.25 | 6.5 | 6.75 | 7.25 | 7.5 | 8.0 | 8.0 | 8.25 | 8.25 | 8.25 |
| | Mortality | 0 | 0 | 0 | 0 | 0 | 0 | 0 | 1/4 | 1/4 | 2/4 | 2/4 | 3/4 | 3/4 | 3/4 |
| 0.2% R-U 0.5% C9 Na⁺ Salt | Phyto | 0 | 0 | 1.0 | 3.0 | 5.75 | 8.0 | 8.75 | 8.75 | 9.75 | 10 | 10 | 10 | 10 | 10 |
| | Mortality | 0 | 0 | 0 | 0 | 0 | 0 | 0 | 0 | 3/4 | 4/4 | 4/4 | 4/4 | 4/4 | 4/4 |
| 0.2% R-U 1.0% C9 Na⁺ Salt | Phyto | 0 | 0 | 2.0 | 4.0 | 7.5 | 9.0 | 9.0 | 10 | 10 | 10 | 10 | 10 | 10 | 10 |
| | Mortality | 0 | 0 | 0 | 0 | 0 | 0 | 0 | 4/4 | 4/4 | 4/4 | 4/4 | 4/4 | 4/4 | 4/4 |

TABLE 7

Corn

| | | Days after Treatment | | | | | | | | | | | | | | | | |
|---|---|---|---|---|---|---|---|---|---|---|---|---|---|---|---|---|---|---|
| | | 2 | 4 | 7 | 9 | 11 | 16 | 18 | 21 | 23 | 25 | 28 | 30 | 32 | 35 | 42 | 46 | 57 |
| 0.2% Round Up | Phyto | 0 | 0 | 0.5 | 0.5 | 1.0 | 1.0 | 1.5 | 1.75 | 1.75 | 2.75 | 3.25 | 3.5 | 4.5 | 6.0 | 6.5 | 6.5 | 7.0 |
| | Mortality | 0 | 0 | 0 | 0 | 0 | 0 | 0 | 0 | 0 | 0 | 0 | 0 | 0 | 0 | 0 | 0 | 0 |
| 0.1% C9 Na⁺ Salt | Phyto | 0 | 0 | 0 | 0 | 0 | 0.25 | 1.0 | 1.0 | 1.0 | 1.0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 | 0 | 0 | 0 |
| 0.5% C9 Na⁺ Salt | Phyto | 0 | 0 | 0 | 0.5 | 0.5 | 1.0 | 1.0 | 1.0 | 1.0 | 1.0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 | 0 | 0 | 0 |
| 1.0% C9 Na⁺ Salt | Phyto | 0 | 0 | 0 | 0 | 0 | 0.25 | 0.25 | 0.5 | 0.75 | 1.0 | 0 | 0 | 0 | 0 | 0 | 0 | 0 |
| | Mortality | 0 | 0 | 0 | 0 | 0 | 0 | 0 | 0 | 0 | 0 | 0 | 0 | 0 | 0 | 0 | 0 | 0 |
| 0.2% R-U 0.1% C9 Na⁺ Salt | Phyto | 0 | 0 | 0 | 0.25 | 1.0 | 2.5 | 2.75 | 2.75 | 2.75 | 3.0 | 2.75 | 2.75 | 3.0 | 3.0 | 4.0 | 3.25 | 4.0 |
| | Mortality | 0 | 0 | 0 | 0 | 0 | 0 | 0 | 0 | 0 | 0 | 0 | 0 | 0 | 0 | 0 | 0 | 0 |
| 0.2% R-U 0.5% C9 Na⁺ Salt | Phyto | 0 | 0 | 1.0 | 1.25 | 1.5 | 2.0 | 2.25 | 2.50 | 2.50 | 2.5 | 2.50 | 2.50 | 3.25 | 3.75 | 4.75 | 4.5 | 4.5 |
| | Mortality | 0 | 0 | 0 | 0 | 0 | 0 | 0 | 0 | 0 | 0 | 0 | 0 | 0 | 0 | 0 | 0 | 0 |
| 0.2% R-U 1.0% C9 Na⁺ Salt | Phyto | 0 | 0 | 1.0 | 2.25 | 3.25 | 5.25 | 5.25 | 6.25 | 7.25 | 7.50 | 8.0 | 8.0 | 8.0 | 8.75 | 9.0 | 9.0 | 9.25 |
| | Mortality | 0 | 0 | 0 | 0 | 0 | 0 | 0 | 0 | 0 | 0 | 0 | 0 | 0 | 2/8 | 5/8 | 6/8 | 6/8 |

TABLE 8

Oats*

| | | Days after Treatment | | | | | | | | | | | | |
|---|---|---|---|---|---|---|---|---|---|---|---|---|---|---|
| | | 2 | 4 | 7 | 9 | 11 | 16 | 18 | 21 | 23 | 25 | 28 | 30 | 32 | 35 |
| 0.2% Round Up | Phyto Mortality | 0 | 0 | 0.75 | 1.0 | 1.5 | 1.75 | 1.5 | 1.5 | 1.75 | 2.25 | 2.0 | 2.0 | 2.0 | 2.5 |
| 0.1% C9 Na⁺ Salt | Phyto Mortality | 0 | 0 | 0 | 0 | 0 | 0 | 0 | 0 | 0 | 0 | 0 | 0 | 0 | 0 |
| 0.5% C9 Na⁺ Salt | Phyto Mortality | 0 | 0 | 0 | 0 | 0 | 0 | 0 | 0 | 0 | 0 | 0 | 0 | 0 | 0 |
| 1.0% C9 Na⁺ Salt | Phyto Mortality | 0 | 0 | 0 | 0 | 0 | 0 | 0 | 0 | 0 | 0 | 0 | 0 | 0 | 0 |
| 0.2% R-U 0.1% C9 Na⁺ Salt | Phyto Mortality | 0 | 0 | 1.0 | 1.0 | 1.5 | 2.0 | 2.0 | 2.0 | 2.0 | 2.0 | 1.25 | 1.25 | 1.5 | 1.5 |
| 0.2% R-U 0.5% C9 Na⁺ Salt | Phyto Mortality | 0 | 0 | 0.75 | 1.5 | 1.75 | 2.0 | 2.0 | 2.0 | 2.0 | 1.75 | 1.0 | 1.0 | 1.5 | 1.5 |
| 0.2% R-U 1.0% C9 Na⁺ Salt | Phyto Mortality | 0 | 0 | 1.0 | 1.5 | 2.25 | 3.0 | 3.25 | 3.25 | 3.25 | 3.5 | 3.25 | 3.5 | 3.75 | 4.0 |

*Note:
No mortality was observed, results presented are phytotoxicity ratings only With respect to the above experiments, it is noted that fatty acid/glyphosate herbicides having glyphosate (Round-Up) concentrations of 0.5 to 1% usually caused so much damage to the test plants (approaching 100%) that evidence of potentiation was lost. The recommended rate of Round-Up for application to established weeds under field conditions is 1 to 2% of the product diluted in water. It is further noted that greenhouse-grown plants are generally more susceptible to lower rates of herbicide than are field-grown plants.

In addition, an enhanced herbicidal effect resulting from the application of a combination herbicide (including glyphosate-based herbicide and fatty acid based herbicide) is not supported in every species in each experiment. There are a number of reasons for this. Primarily, though, in herbicidal experiments, the conditions under which the plants are grown (light, temperature and humidity), the age of the plants, the species and variety of plant, and the rate and method of application of herbicidal components all can influence the ratios at which enhanced herbicidal activity is observed. In addition, a test method selected may, in some cases, be so hypersensitive that the additive effect of the two active ingredient components results in plant death. Therefore potentiation cannot always be detected.

It is understood that variations may be made to the herbicidal compositions disclosed herein without departing from the spirit and scope of the invention.

What is claimed is:

1. An aqueous herbicidal composition, comprising:
a glyphosate-based component selected from the group consisting of N-(phosphonomethyl)glycine and salts thereof, present at a concentration in the range of about 0.08 to 2.0 percent by weight of a ready-to-use composition; and
a saponified or non-saponified fatty acid-based active ingredient present at a concentration in the range of about 0.5 to less than 3.0 percent by weight of a ready-to-use composition, said fatty acid-based active ingredient comprising a mixture of pelargonic acid, capric acid and lauric acid or salts thereof.

2. The composition of claim 1 wherein the glyphosate-based component comprises the isopropyl amine salt of N-(phosphonomethyl)glycine.

3. The composition of claim 1 wherein said fatty acid-based active ingredient comprises a mixture of salts of pelargonic acid, capric acid and lauric acid.

4. The composition of claim 3 wherein said fatty acid-based active ingredient additionally comprises a salt of a fatty acid selected from the group consisting of caprylic acid, undecanoic acid, oleic acid and mixtures thereof.

5. The composition of claim 4 wherein said fatty acid-based active ingredient comprises a mixture of salts of pelargonic acid, capric acid, lauric acid and a salt of a fatty acid mixture selected from the group consisting of soybean fatty acid and coconut fatty acid.

6. The composition of claim 1 wherein said fatty acid-based active ingredient comprises a mixture of salts of pelargonic acid, capric acid and lauric acid selected from the group consisting of metal salts and ammonium salts.

7. The composition of claim 6 wherein said fatty acid-based active ingredient comprises a mixture of sodium salts of pelargonic acid, capric acid and lauric acid.

8. The composition of claim 6 wherein said fatty acid-based active ingredient comprises a mixture of potassium salts of pelargonic acid, capric acid and lauric acid.

9. The composition of claim 1 wherein said fatty acid-based active ingredient additionally comprises an emulsifier component.

10. The composition of claim 1 wherein said fatty acid-based active ingredient comprises a mixture of sodium or potassium salts of pelargonic acid, capric acid and lauric acid, the fatty acid salts being present at a weight ratio of about 1:1:2, respectively.

11. A method of controlling the growth of unwanted vegetation, comprising the step of applying the herbicidal composition of claim 1 to the unwanted vegetation at a volume of 47 to 374 liters per hectare.

* * * * *